United States Patent [19]

Bowers

[11] 4,410,512

[45] Oct. 18, 1983

[54] COMBINATIONS HAVING SYNERGISTIC PITUITARY GROWTH HORMONE RELEASING ACTIVITY

[75] Inventor: Cyril Y. Bowers, New Orleans, La.

[73] Assignee: Beckman Instruments, Inc., Fullerton, Calif.

[21] Appl. No.: 334,488

[22] Filed: Dec. 28, 1981

[51] Int. Cl.$^3$ ............................................. A61K 37/02
[52] U.S. Cl. ..................................................... 424/177
[58] Field of Search ................... 260/112.5 R; 424/177

[56] References Cited

U.S. PATENT DOCUMENTS

| | | | |
|---|---|---|---|
| 3,239,345 | 3/1966 | Hodge et al. | 424/279 |
| 4,036,979 | 7/1977 | Asato | 424/275 |
| 4,223,020 | 9/1980 | Momany | 260/112.5 R |
| 4,223,021 | 9/1980 | Momany | 260/112.5 R |
| 4,224,316 | 9/1980 | Momany | 260/112.5 R |
| 4,226,857 | 10/1980 | Momany | 260/112.5 R |
| 4,228,155 | 10/1980 | Momany | 260/112.5 R |
| 4,228,156 | 10/1980 | Momany | 260/112.5 R |
| 4,228,157 | 10/1980 | Momany | 260/112.5 R |
| 4,228,158 | 10/1980 | Momany | 260/112.5 R |

*Primary Examiner*—Delbert R. Phillips
*Assistant Examiner*—F. T. Moezie
*Attorney, Agent, or Firm*—Robert J. Steinmeyer; John E. Vanderburgh; Robert S. Frieman

[57] ABSTRACT

Novel combinations comprising (a) at least one peptide having the following amino acid sequence

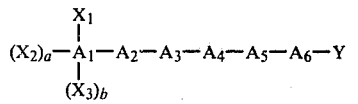

wherein $X_1$, $X_2$, and $X_3$ are selected from a group consisting of N-terminal and desamino alpha-carbon substitutions and a and b are 0 or 1, provided that a and b are always 0 when $A_1$ is a desamino residue; $A_1$ and $A_4$ are selected from a group consisting of histidyl, arginyl, lysyl, α-naphthylalanyl, β-naphthylalanyl, isoquinolyl, tyrosyl, tryptophyl, phenylalanyl, homologues and analogues thereof, and, with respect to $A_1$ only the desamino forms thereof; $A_2$ and $A_5$ are selected from a group consisting of D-histidyl, D-arginyl, D-lysyl, D-α-naphthylalanyl, D-β-naphthylalanyl, D-isoquinolyl, D-tyrosyl, D-tryptophyl, D-phenylalanyl, homologues and analogues thereof; $A_3$ is selected from a group consisting of glycyl, alanyl, valyl, leucyl, isoleucyl, prolyl, seryl, threonyl, methionyl, aspartyl, glutamyl, asparginyl, glutaminyl, histidyl, D-alanyl, D-valyl, D-leucyl, D-isoleucyl, D-prolyl, D-seryl, D-threonyl, D-methionyl, D-aspartyl, D-glutamyl, D-asparaginyl, D-glutaminyl, D-histidyl, and homologues and analogues thereof; $A_6$ is selected from a group consisting of amino acids of the L- and D- configuration, homologues and analogues thereof, and the decarboxy forms thereof; and Y is selected from a group consisting of C-terminal and descarboxy alpha-carbon substitutions; and the pharmaceutically acceptable salts thereof; and (b) a growth promoting agent.

3 Claims, No Drawings

COMBINATIONS HAVING SYNERGISTIC PITUITARY GROWTH HORMONE RELEASING ACTIVITY

BACKGROUND OF THE INVENTION

1. Field of the Invention

This invention relates to combinations comprising at least one peptide and at least one growth promoting agent, which combination possesses synergistic pituitary growth hormone releasing activity.

2. Description of the Prior Art

Growth hormone, which is secreted from the pituitary, causes growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as some instances of dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalmus perhaps either to decrease somatostatin secretion or to increase an unknown endogenous growth hormone-releasing hormone or both.

Compounds which directly act on the pituitary to release growth hormone include prostaglandin $E_1$ and $E_2$, theophylline, and cyclic nucleotides. However, these compounds neither specifically release growth hormone nor are they believed to act at the putative growth hormone-releasing hormone receptors in the peripheral membrane of the pituitary cell to initiate growth hormone release.

In addition, under special conditions certain chemically defined peptides, e.g., vasopressin, thyroid-releasing hormone (TRH), luteinizing hormone-releasing hormone (LH-RH), α-melanocyte-stiumulating hormone (α-MSH), glucagon, substance P, neurotensin; Met-enkephalin, β-endorphin, cholera-enderotoxin, and basic myelin protein, act to release growth hormone from the pituitary. However, only TRH acts directly on the pituitary to elicit this response. Furthermore, the above listed peptides release other pituitary hormones and under most experimental conditions do not release growth hormone. For example, TRH does not release growth hormone in normal rats or in normal humans or from pituitaries of normal rats or monkeys. In vitro, TRH releases growth hormone, prolactin, and thyroid stimulating hormone (TSH) in certain species, and, in vivo, TRH releases these hormones from bovine pituitary.

Vasopressin's induced release of growth hormone is considered to be due to a non-specific response to stress caused by administration of high dosages of vasopressin.

Accordingly it would be highly desirable to have a compound or combination of compounds which directly acts on the pituitary under normal experimentatal conditions to effect the release of growth hormone therefrom. Such compound or combination of compounds would be useful in vitro, e.g., as unique research tools for understanding how growth hormone secretion is regulated at the pituitary level and could also be useful in vivo, e.g., to treat symptoms related to growth hormone deficiencies, to increase the rate and extent of growth in commercial animals, to increase milk yield in commercial animals, and to reduce the number of mucosal erosions induced by hypoxemia.

SUMMARY OF THE INVENTION

In accordance with the present invention there is provided a combination of compounds which act directly on the pituitary under normal experimental conditions in vitro to synergisticly release growth hormone therefrom.

These growth hormone releasing combinations can be utilized in vitro as unique research tools for understanding, inter alia, how growth hormone secretion is regulated at the pituitary level.

More particularly, this invention encompasses a combination of compounds comprising (a) at least one peptide having the formula I

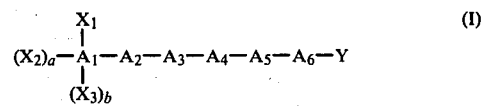

wherein $X_1$, $X_2$, and $X_3$ are selected from a group consisting of N-terminal and desamino alpha-carbon substitutions; a and b are 0 or 1, provided that a and b are always 0 when $A_1$ is a desamino residue; $A_1$ and $A_4$ are selected from a group consisting of histidyl, arginyl, lysyl, α-naphthylalanyl, β-naphthylalanyl, isoquinolyl, tyrosyl, tryptophyl, phenylalanyl, homologues and analogues thereof, and, with respect to $A_1$ only, the desamino forms thereof; $A_2$ and $A_5$ are selected from a group consisting of D-histidyl, D-arginyl, D-lysyl, D-α-naphthylalanyl, D-β-naphthylalanyl, D-isoquinolyl, D-tyrosyl, D-tryptophyl, D-phenylalanyl, homologues and analogues thereof, and, with respect to $A_5$ only, the descarboxy forms thereof; $A_3$ is selected from a group consisting of glycyl, alanyl, valyl, leucyl, isoleucyl, prolyl, seryl, threonyl, methionyl, aspartyl, glutamyl, asparaginyl, glutaminyl, histidyl, D-alanyl, D-valyl, D-leucyl, D-isoleucyl, D-prolyl, D-seryl, D-threonyl, D-methionyl, D-aspartyl, D-glutamyl, D-asparaginyl, D-glutaminyl, D-histidyl, and homologues and analogues thereof; $A_6$ is selected from a group consisting of amino acids of the L- and D-configuration, homologues and analogues thereof, and the descarboxy forms thereof; and Y is selected from a group consisting of C-terminal and descarboxy alpha-carbon substitutions; and the pharmaceutically acceptable salts thereof; and (b) at least one growth promoting agent.

DETAILED DESCRIPTION OF THE PREFERRED EMBODIMENTS

The peptide moiety of this invention has the amino acid residue sequence represented by formula I, supra.

All amino acid residues identified herein are in the natural or L-configuration unless otherwise specified.

Abbreviations for amino acid residues are used in accordance with the following standard peptide nomenclature:

| | | | |
|---|---|---|---|
| Tyr | L-tyrosyl | Ile | L-isoleucyl |
| D-Tyr | D-tyrosyl | D-Ile | D-isoleucyl |
| Gly | glycyl | Leu | L-leucyl |
| Phe | L-phenylalanyl | D-Leu | D-leucyl |
| D-Phe | D-phenylalanyl | Thr | L-threonyl |
| Met | L-methionyl | D-Thr | D-threonyl |
| D-Met | D-methionyl | Val | L-valyl |
| Ala | L-alanyl | D-Val | D-valyl |
| D-Ala | D-alanyl | Pro | L-prolyl |
| Ser | L-seryl | D-Pro | D-prolyl |
| D-Ser | D-seryl | Gln | L-glutaminyl |
| Lys | L-lysyl | D-Gln | D-glutaminyl |
| D-Lys | D-lysyl | Glu | L-glutamyl |
| Asn | L-asparaginyl | D-Glu | D-glutamyl |
| D-Asn | D-asparaginyl | Trp | L-tryptophyl |
| His | L-histidyl | D-trp | D-tryptophyl |
| | | L-Asp | L-aspartyl |
| D-His | D-histidyl | D-Asp | D-aspartyl |
| Cys | L-cysteinyl | Arg | L-arginyl |
| D-Cys | D-cysteinyl | D-Arg | D-arginyl |
| Hypro | L-hydroxyprolyl | | |
| D-Hypro | D-hydroxyprolyl | | |
| Dopa | L-3,4-dihydroxy-phenylalanyl | L-<Glu | L-pyroglutamyl |
| D-Dopa | D-3,4-dihydroxy-phenylalanyl | D-<Glu | D-pyroglutamyl |
| Hylys | L-δ-hydroxylysyl | Sar | N—methylglycyl (sarcosyl) |
| D-Hylys | D-δ-hydroxylysyl | | |
| Aib | L-α-methylalanyl (L-aminoisobutyryl) | α-Naphth | L-α-naphthyl-alanyl |
| | | D-α-Naphth | D-α-naphthyl-alanyl |
| | | β-Naphth | L-β-naphthyl-alanyl |
| Iql | L-isoquinolyl | D-β-Naphth | D-β-naphthyl-alanyl |
| D-Iql | D-isoquinolyl | | |

Virtually any suitable N-terminal and desamino alpha-carbon substitution can be used in the instant invention as represented by the various structural formulas set forth herein. Typical N-terminal and desamino alpha-carbon substitutions include, but are not limited to, those also set forth in Table I.

TABLE I

| N—Terminus and Desamino Alpha-Carbon Substitutions[1] | | | | |
|---|---|---|---|---|
| N—Terminus Substitutions | | | | |
| $X_1$ | $X_2$ | $X_3$ | a | b |
| $R_1-$ | $R_2-$ | — | 1 | 0 |
| $R_1-$ | $R_2-$ | $R_3-$ | 1 | 1 |
| $R_1-Z-\overset{O}{\underset{\|}{C}}-$ | $R_2-$ | — | 1 | 0 |
| $R_1-\overset{O}{\underset{\|}{C}}-$ | $R_2-$ | — | 1 | 0 |
| $R_1-$ | HO— | — | 1 | 0 |
| $R_1-\underset{\|}{N}-\overset{R_2}{}$ | $R_3-$ | — | 1 | 0 |
| $R_1-\underset{\|}{N}-\overset{R_2}{}\overset{Z}{\underset{\|}{C}}-$ | $R_3-$ | — | 1 | 0 |
| R— | — | — | 0 | 0 |

TABLE I-continued

| N—Terminus and Desamino Alpha-Carbon Substitutions[1] | | | | |
|---|---|---|---|---|
| N—Terminus Substitutions | | | | |
| $X_1$ | $X_2$ | $X_3$ | a | b |
| RZ— | — | — | 0 | 0 |

[1]LEGEND: R, $R_1$, $R_2$, and $R_3$ are selected from a group consisting of hydrogen; straight and branched chain lower alkyl groups having from 1 to 6 carbon atoms; cycloalkyl groups having from 3 to 6 carbon atoms; benzyl; benzhydryl; trityl; aryl; alkoxybenzyl; alkoxybenzhydryl; alkoxytrityl; lower haloalkyl groups having from 1 to 6 carbon atoms; halobenzyl; halobenzhydryl; halotrityl; haloaryl; and cyclohaloalkyl groups having from 3 to 6 carbon atoms. Preferably, R, $R_1$, $R_2$, and $R_3$ are selected from the group consisting of hydrogen and alkyl groups having from 1 to 6 carbon atoms. More preferably, R, $R_1$, $R_2$, and $R_3$ are selected from the group consisting of hydrogen and alkyl groups having 1 to 2 carbon atoms.
Z is selected from a group consisting of oxygen and sulfur. Z is preferably oxygen.

Virtually any suitable C-terminal and descarboxy alpha-carbon substitution can be used in the instant invention as represented by the various structural formulas set forth herein. Typical C-terminal and descarboxy alpha-carbon substitutions include, but are not limited to, those also set forth in Table II.

TABLE II

C—Terminus and Descarboxy Alpha-Carbon Substitutions[1]

C—Terminus Substitutions

—OR $-\underset{\|}{N}-R_2$ with $R_1$

—R $-\underset{\underset{R_3}{\|}}{\overset{R_1}{\|}}C-R_2$ $-\underset{\|}{N}-\underset{\|}{N}-R_3$ with $R_1$, $R_2$ $-\underset{\|}{N}-\underset{\|}{N}-\overset{O}{\underset{\|}{C}}-R_3$ with $R_1$, $R_2$ Descarboxy Alpha-Carbon Substitutions

—R $-\underset{\underset{R_3}{\|}}{\overset{R_1}{\|}}C-OR_2$ $-\underset{\underset{R_3}{\|}}{\overset{VR_1}{\|}}C-VR_2$ $-\overset{NH}{\underset{\|}{C}}-\underset{\|}{N}-R_2$ with $R_1$ $-C\underset{\diagdown}{\diagup}\overset{N=N}{\underset{N-N}{\|}}$
       |
       R $-C\underset{\diagdown}{\diagup}\overset{N-N-R}{\underset{N=N}{\|}}$

TABLE II-continued $$-C=N^+-R_1$$
$$\quad\quad | \quad\quad\ |$$
$$\quad\quad\ \ R_2$$
$$\quad\quad\ \ |$$
$$\quad\quad\ \ O-R_3$$

[1]LEGEND: R, $R_1$, $R_2$, and $R_3$ are as defined in Table I, supra.
V is selected from a group consisting of oxygen, sulfur, and nitrogen. V is preferably oxygen.

The structure of amino acid residues employed in the peptide moiety of this invention are set forth in Table III. Typical homologues and analogues of these amino acid residues which can also be employed in the peptide moiety of this invention include, but are not limited to, those listed in Table III.

TABLE III

L or D Amino Acid Residue

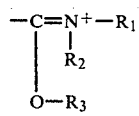

| NAME | NATURAL SUBSTITUENTS | | | SUBSTITUENTS OF HOMOLOGUES & ANALOGUES[1] | | |
|---|---|---|---|---|---|---|
|  | $R_a$ | $R_b$ | $R_c$ | $R_a$ | $R_b$ | $R_c$ |
| Gly | —H | —H | —H | —H | U | $U_1$ |
| Ala | —CH$_3$ | —H | —H | —CH$_3$ | U | $U_1$ |
|  |  |  |  | =CH$_2$ | — | U |
| Val | —CH(CH$_3$)$_2$ | —H | —H | —CH(CH$_3$)$_2$ | U | $U_1$ |
|  |  |  |  | —C(CH$_3$)$_3$ | U | $U_1$ |
|  |  |  |  | =C(CH$_3$)$_2$ | — | U |
| Leu | —CH$_2$CH(CH$_3$)$_2$ | —H | —H | —(CH$_2$)$_{n+1}$CH(CH$_3$)$_2$ | U | $U_1$ |
|  |  |  |  | —(CH$_2$)$_{n+1}$C(CH$_3$)$_3$ | U | $U_1$ |
|  |  |  |  | =CHCH(CH$_3$)$_2$ | — | U |
|  |  |  |  | =CH(CH$_2$)$_n$CH(CH$_3$)$_2$ | — | U |
| Ile | CH$_3$<br>\|<br>—CH—C$_2$H$_5$ | —H | —H | CH$_3$<br>\|<br>—CH—C$_2$H$_5$ | U | $U_1$ |
| NIle | —CH$_2$CH$_2$CH$_2$CH$_3$ | —H | —H | —(CH$_2$)$_{n+1}$CH$_3$ | U | $U_1$ |
|  |  |  |  | =CH(CH$_2$)$_n$CH$_3$ | — | U |
| Pro | CH$_2$—CH$_2$—CH$_2$<br>\|              —H              \| | | | CH$_2$——(CH$_2$)$_n$——CH$_2$<br>\|              U              \| | | |
|  |  |  |  | CH$_2$——CH══════CH<br>\|              U              \| | | |
|  |  |  |  | CH$_2$——CHOU——CH$_2$<br>\|              $U_1$              \| | | |
|  |  |  |  | (CH$_2$)$_n$——B——(CH$_2$)<br>\|              U              \| | | |
| Ser | —CH$_2$OH | —H | —H | —(CH$_2$)$_{n+1}$OU | $U_1$ | $U_2$ |
| Thr | —CHOH—CH$_3$ | —H | —H | —(CH$_2$)$_{n+1}$CHOU—CH$_3$ | $U_1$ | $U_2$ |
| Cys | —CH$_2$SH | —H | —H | —(CH$_2$)$_{n+1}$SU | $U_1$ | $U_2$ |
|  |  |  |  | —(CH$_2$)$_{n+1}$SO$_3$H | U | $U_1$ |
| Met | —CH$_2$CH$_2$SCH$_3$ | —H | —H | —(CH$_2$)$_{n+1}$SCH$_3$ | U | $U_1$ |
|  |  |  |  | =CH(CH$_2$)$_{n+1}$SCH$_3$ | — | $U_1$ |
|  |  |  |  | —(CH$_2$)$_{n+1}$SOCH$_3$ | U | $U_1$ |
|  |  |  |  | =CH(CH$_2$)$_{n+1}$SOCH$_3$ | — | $U_1$ |
|  |  |  |  | —(CH$_2$)$_{n+1}$SO$_2$CH$_3$ | U | $U_1$ |
|  |  |  |  | =CH(CH$_2$)$_{n+1}$SO$_2$CH$_3$ | — | U |
| Asp | —CH$_2$CO$_2$H | —H | —H | —(CH$_2$)$_{n+1}$CO$_2$U | $U_1$ | $U_2$ |
|  |  |  |  | =CH(CH$_2$)$_n$CO$_2$U | — | $U_1$ |
| Glu | —(CH$_2$)$_2$CO$_2$H | —H | —H | —(CH$_2$)$_{n+1}$CO$_2$U | $U_1$ | $U_2$ |
| Asn | —CH$_2$CONH$_2$ | —H | —H | —(CH$_2$)$_{n+1}$CONR$_1$R$_2$ | U | $U_1$ |
|  |  |  |  | =CH(CH$_2$)$_n$CONR$_1$R$_2$ | — | U |
| Gln | —(CH$_2$)$_2$CONH$_2$ | —H | —H | —(CH$_2$)$_{n+1}$CONR$_1$R$_2$ | U | $U_1$ |
| Arg | —(CH$_2$)$_3$NH—C=NH<br>\|<br>NH$_2$ | —H | —H | —(CH$_2$)$_{n+1}$NU—C=ND<br>\|<br>N—D$_1$<br>\|<br>D$_2$ | $U_1$ | $U_2$ |

TABLE III-continued

L or D Amino Acid Residue $$-N(R_c)-C(R_a)(R_b)-C(=O)-$$

| NAME | NATURAL SUBSTITUENTS $R_a$ | $R_b$ | $R_c$ | SUBSTITUENTS OF HOMOLOGUES & ANALOGUES[1] $R_a$ | $R_b$ | $R_c$ |
|---|---|---|---|---|---|---|
| | | | | $-(CH_2)_{n+1}NUC(N-D_1)=\overset{+}{N}(D_3)-D_2$ | $U_1$ | $U_2$ |
| Lys | $-(CH_2)_4NH_2$ | $-H$ | $-H$ | $-(CH_2)_{n+1}N(U_1)-U_2$ | U | $U_3$ |
| | | | | $-(CH_2)_{n+1}\overset{+}{N}(U_1)(U_3)-U_2$ | U | $U_4$ |
| His | $-CH_2-$[imidazole with NH, N] | $-H$ | $-H$ | $-(CH_2)_{n+1}-$[imidazole N—D, N] | U | $U_1$ |
| | | | | $-(CH_2)_{n+1}-$[imidazole N, N—D] | U | $U_1$ |
| | | | | $-(CH_2)_{n+1}-$[imidazole N—D, +N—D] | U | $U_1$ |
| | | | | $-(CH_2)_{n+1}-$[imidazole N, N=D] | U | $U_1$ |
| | | | | $-(CH_2)_{n+1}-$[pyrazole N, N—D] | U | $U_1$ |
| | | | | $-(CH_2)_{n+1}-$[pyrazole D-N, N] | U | $U_1$ |
| | | | | $-(CH_2)_{n+1}-$[pyrazole N, N—D] | U | $U_1$ |
| | | | | $-(CH_2)_{n+1}-$[ring with L, B] | U | $U_1$ |
| | | | | $-(CH_2)_{n+1}-$[ring with B, L] | U | $U_1$ |
| | | | | $-(CH_2)_{n+1}-$[ring with L, B] | U | $U_1$ |

TABLE III-continued

L or D Amino Acid Residue $$-N(R_c)-C(R_a)(R_b)-C(=O)-$$

| NAME | NATURAL SUBSTITUENTS | | | SUBSTITUENTS OF HOMOLOGUES & ANALOGUES[1] | | |
|------|---------------------|-----|-----|----------------------------------------|-----|-----|
|      | $R_a$ | $R_b$ | $R_c$ | $R_a$ | $R_b$ | $R_c$ |
|      |      |     |     | $-(CH_2)_{n+1}$—(cyclic B=L) | U | $U_1$ |
|      |      |     |     | $-(CH_2)_{n+1}$—(cyclic L–B) | U | $U_1$ |
|      |      |     |     | imidazole-CH$_2$– with N–D and CH$_2$–U | | |
|      |      |     |     | imidazole-CH$_2$– with D-N and CH$_2$–U | | |
| Phe  | $-CH_2-C_6H_5$ | –H | –H | $-(CH_2)_{n+1}$–(ring $K_1=K_2, K_3, K_5=K_4$) | U | $U_1$ |
|      |      |     |     | $=CH(CH_2)_n$–(ring $K_1=K_2, K_3, K_5=K_4$) | — | $U_1$ |
|      |      |     |     | (ring $K_1=K_2-K_3=K_4$) with two CH$_2$ | | $U_1$ |
| Tyr  | $-CH_2-C_6H_4-OH$ | –H | –H | See Phe above | | |

TABLE III-continued

L or D Amino Acid Residue $$-\text{N}(R_c)-\text{C}(R_a)(R_b)-\text{C}(=\text{O})-$$

| NAME | NATURAL SUBSTITUENTS $R_a$ | $R_b$ | $R_c$ | SUBSTITUENTS OF HOMOLOGUES & ANALOGUES[1] $R_a$ | $R_b$ | $R_c$ |
|---|---|---|---|---|---|---|
| α-Naphth | —CH$_2$—(1-naphthyl) | —H | —H | —(CH$_2$)$_{n+1}$—[K$_1$..K$_7$ ring] | U | U$_1$ |
| | | | | =CH—[K$_1$..K$_7$ ring] | — | U |
| β-Naphth | —CH$_2$—(2-naphthyl) | —H | —H | —(CH$_2$)—[K$_1$..K$_7$ ring] | U | U$_1$ |
| | | | | =CH—[K$_1$..K$_7$ ring] | — | U |
| Trp | —CH$_2$—(indolyl) | —H | —H | —(CH$_2$)$_{n+1}$—[K$_1$..K$_4$, L ring] | U | U$_1$ |
| Sar | —H | —H | —CH$_3$ | U | U$_1$ | —CH$_3$ |
| Iql | —CH$_2$—(isoquinolinyl) | —H | —H | —(CH$_2$)$_{n+1}$—[K$_1$..K$_4$, L ring] | U | U$_1$ |

[1]LEGEND: U, U$_1$, U$_2$, U$_3$ and U$_4$ are selected from a group consisting of hydrogen, alkyl groups having from 1–10 carbon atoms, and benzyl.
B, B$_1$, and B$_2$ are selected from a group consisting of —N—D, O, S.
D, D$_1$, D$_2$, and D$_3$ are selected from a group consisting of hydrogen, methyl, ethyl, propyl, benzyl, formyl, and tosyl.
K$_1$, K$_2$, K$_3$, K$_4$, K$_5$, K$_6$, and K$_7$ are N or —C—G, provided that adjacent positions are not both N.
G is selected from a group consisting of hydrogen, halogen, —OU, —OR$_x$, —SR$_x$, —R$_x$, —SO$_3$R$_x$, —B(OH)$_2$, —NR$_x$SOR$_y$, —NR$_x$R$_y$, —C≡N, —N(R$_x$)COR$_y$, —SOR$_x$, —SO$_2$R$_x$, —SO$_2$, —CO$_2$R$_x$, —CONR$_x$R$_y$, —CONR$_x$COR$_y$, wherein R$_x$ and R$_y$ are selected from a group consisting of hydrogen and straight and branched alkyl groups containing 1–6 carbon atoms, and substituted straight and branched alkyl groups containing 1–6 carbon atoms, wherein the substituents include, but are not limited to, one or more halo, hydroxy, amino, and mercapto groups.
L is —N or —N$^+$—D.
R$_1$ and R$_2$ are as defined in Table I.
n is an integer from 0 to 4.

The term "pharmaceutically acceptable salts", as used herein, refers to the non-toxic alkali metal, alkaline earth metal and ammonium salts commonly used in the pharmaceutical industry including, but not limited to, the sodium, potassium, lithium, calcium, magnesium, barium, ammonium and protamine salts which are prepared by methods well known in the art. The term also includes non-toxic acid addition salts which are generally prepared by reacting the compounds of this invention with a suitable organic or inorganic acid. Representative salts include, but are not limited to, the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

Preferably, the peptide moiety of this invention has the amino acid sequence represented by formula I, supra, wherein a is 0 or 1, b is 0 and X$_1$ and X$_2$ are selected from a group consisting of —R, —OR, and RC(O)—, wherein R is selected from a group consisting of hydrogen and straight and branched chain alkyl groups containing 1–6 carbon atoms; A$_1$ and A$_4$ are selected from the group consisting of histidyl, tryptophyl, phenylalanyl, tyrosyl, homologues and analogues thereof, and, with respect to A$_1$, the desamino forms thereof; A$_2$ and A$_5$ are selected from the group consisting of D-histidyl, D-tryptophyl, D-phenylalanyl, D-tyrosyl, homologues and analogues thereof; $A_3$ is selected from the group consisting of glycyl, alanyl, seryl, asparaginyl, prolyl, D-alanyl, D-seryl, D-asparaginyl, D-prolyl, and homologues and analogues thereof; $A_6$ is selected from the group consisting of arginine, lysine, ornithine, histidine, aspartic acid, glutamic acid, asparagine, glutamine, D-arginine, D-lysine, D-ornithine, D-histidine, D-aspartic acid, D-glutamic acid, D-asparagine, D-glutamine, D-arginine, homologues and analogues thereof, and the descarboxy forms thereof; Y is selected from a group consisting of —CH₂OH, —OR, and —NR₁R₂, wherein R, $R_1$, and $R_2$ are selected from a group consisting of hydrogen and straight and branched chain alkyl groups containing 1-6 carbon atoms; and the pharmaceutically acceptable salts thereof.

More preferably, the peptide moiety of this invention has the amino acid sequence represented by formula II:

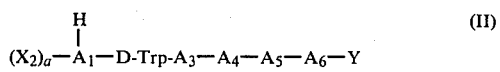
$$(X_2)_a - A_1 - D\text{-}Trp\text{-}A_3 - A_4 - A_5 - A_6 - Y \qquad (II)$$

wherein a is 0 or 1; $X_2$ is selected from the group consisting of R— and RC(O)—; wherein R is selected from the group consisting of hydrogen and alkyl groups containing 1-2 carbon atoms; $A_1$ is selected from the group consisting of tyrosyl, O-methyltyrosyl, histidyl, 3-N-methylhistidyl, p-chlorophenylalanyl, and the desamino forms thereof; $A_3$ is selected from the group consisting of alanyl, seryl, and D-alanyl; $A_4$ is selected from the group consisting of tryptophyl and tyrosyl; $A_5$ is selected from the group consisting of D-phenylalanyl, D-histidyl, D-tyrosyl, and D-p-chlorophenylalanyl; $A_6$ is selected from the group consisting of arginine, homoarginine, lysine, ornithine, aspartic acid, glutamic acid, asparagine, glutamine, and D-lysine; and Y is selected from the group consisting of —OR and —NHR, wherein R is selected from the group consisting of hydrogen and alkyl groups containing 1-2 carbon atoms; and the pharmaceutically acceptable salts thereof.

Peptide moieties within the scope of the instant invention include, but are not limited to, those set forth in Table IV and the desamino and/or descarboxy forms thereof, wherein the respective positions of $X_1$, $X_2$, $X_3$ are set forth in formula I.

using standard solid-phase techniques. The solid-phase synthesis, for example, can be commenced from the C-terminal end of the peptide using an α-amino protected amino acid. A suitable starting material can be prepared, for instance, by attaching the required α-amino acid to a chloromethyl resin, a hydroxymethyl resin, a benzhydrylamine (BHA) resin, or a p-methylbenzylhydrylamine (p-Me-BHA) resin. One such chloromethyl resin is sold under the tradename BIO-BEADS SX-1 by Bio Rad Laboratories, Richmond, Calif. The preparation of the hydroxymethyl resin is described by Bodansky et al., *Chem. Ind.* (London) 38, 1597 (1966). The BHA resin has been described by Pietta and Marshall, *Chem. Commn.* 650 (1970) and is commercially available from Beckman Instruments, Inc., Palo Alto, Calif. in the hydrochloride form thereof (BHA.HCl).

In the solid-phase preparation of the compounds of this invention, a protected amino acid can be coupled to a resin with the aid of a coupling agent. After the initial coupling, the α-amino protecting group can be removed by a choice of reagents including trifluoroacetic acid (TFA) or hydrochloric acid (HCl) solutions in organic solvents at room temperature. After removal of the α-amino protecting group, the remaining protected amino acids can be coupled stepwise in the desired order. Each protected amino acid can be generally reacted in about a 3-fold excess using an appropriate carboxyl group activator such as dicyclohexylcarbodiimide (DCC) in solution, for example, in methylene chloride(CH₂Cl₂)-dimethylformamide (DMF) mixtures.

After the desired amino acid sequence has been completed, the desired peptide can be cleaved from the resin support by treatment with a reagent such as hydrogen fluoride (HF) which not only cleaves the peptide from the resin, but also cleaves all remaining side-chain protecting groups. When a chloromethyl resin or hydroxymethyl resin is used, HF treatment results in the formation of the free peptide acids of Formula I (Y=—COOH). When the BHA or p-Me-BHA resin is used, HF treatment results directly in the free peptide amides of Formula I (Y=—CONH₂). Alternatively, when the chloromethylated or hydroxymethyl resin is employed, the side-chain protected peptide can be cleaved from the resin by treatment of the peptide-resin with ammonia to give the desired side-chain protected amide or

TABLE IV

| |
|---|
| $(X_1—,(X_2—)_a,(X_3—)_b)$—His—D-Trp—Ala—Trp—D-Phe—Lys—Y |
| $(X_1—,(X_2—)_a,(X_3—)_b)$—His—D-5-Br—Trp—Ala—Trp—D-Phe—Lys—Y |
| $(X_1—,(X_2—)_a,(X_3—)_b)$—His—D-Trp—Ala—5-Br—Trp—D-Phe—Lys—Y |
| $(X_1—,(X_2—)_a,(X_3—)_b)$—1-N—Me—His—D-Trp—Ala—Trp—D-Phe—Asn—Y |
| $(X_1—,(X_2—)_a,(X_3—)_b)$—3-N—Me—His—D-Trp—Ala—Trp—D-Phe—Lys—Y |
| $(X_1—,(X_2—)_a,(X_3—)_b)$—Arg—D-Trp—Ala—Iql—D-Phe—Arg—Y |
| $(X_1—,(X_2—)_a,(X_3—)_b)$—Lys—D-Trp—Ala—Trp—D-Phe—Glu—Y |
| $(X_1—,(X_2—)_a,(X_3—)_b)$—His—D-Trp—Ser—Trp—D-Phe—Lys—Y |
| $(X_1—,(X_2—)_a,(X_3—)_b)$—Tyr—D-Trp—D-Ala—Trp—D-His—Gln—Y |
| $(X_1—,(X_2—)_a,(X_3—)_b)$—Tyr—D-Trp—Ala—Trp—D-1-N—Me—His—Met—Y |
| $(X_1—,(X_2—)_a,(X_3—)_b)$—Tyr—D-Trp—Ala—Trp—D-3-N—Me—His—Pro—Y |
| $(X_1—,(X_2—)_a,(X_3—)_b)$—Tyr—D-Trp—Ala—Trp—D-Arg—His—Y |
| $(X_1—,(X_2—)_a,(X_3—)_b)$—Tyr—D-Trp—Ala—Trp—D-Lys—Ser—Y |
| $(X_1—,(X_2—)_a,(X_3—)_b)$—Tyr—D-Trp—D-Ser—Trp—D-Lys—Phe—Y |
| $(X_1—,(X_2—)_a,(X_3—)_b)$—His—D-Trp—Ala—Trp—D-His—Trp—Y |
| $(X_1—,(X_2—)_a,(X_3—)_b)$—Arg—D-Phe—Val—Tyr—D-Lys—D-Lys—Y |
| $(X_1—,(X_2—)_a,(X_3—)_b)$—Tyr—D-Tyr—Met—Phe—D-Arg—D-Orn—Y |
| $(X_1—,(X_2—)_a,(X_3—)_b)$—Phe—D-Phe—Gln—Phe—D-1-N—Me—His—D-Asp—Y |
| $(X_1—,(X_2—)_a,(X_3—)_b)$—His—D-Trp—Ile—Tyr—D-Trp—D-Glu—Y |
| $(X_1—,(X_2—)_a,(X_3—)_b)$—α-Naphth-D-Trp—D-Ala—β-Naphth-D-Phe—Val—Y |
| $(X_1—,(X_2—)_a,(X_3—)_b)$—β-Naphth-D-Lys—D-His—His—D-Arg—Thr—Y |

The peptide moiety of the instant invention can be prepared by solution methods known in the art or by with an alkylamine to give a side-chain protected alkylamide or dialkylamide. Side-chain protection can then be removed in the usual fashion by treatment with HF to give the free peptide amides, alkylamides, or dialkylamides.

In preparing the peptide ester moieties of this invention, the resins used to prepare the acids of Formula I (Y=—COOH) can be employed and the side-chain protected peptide can be cleaved with a base and an appropriate alcohol, i.e., methanol. Side-chain protecting groups can then be removed in the usual fashion by treatment with HF to obtain the desired ester.

The solid-phase procedure discussed above is well known in the art and has been essentially described by Stewart and Young, *Solid Phase Peptide Synthesis*, Freeman and Co., San Francisco (1969).

Some of the well known solution methods which can be employed to synthesize the peptide moieties of the instant invention are set forth in Bodansky et al., *Peptide Synthesis*, 2nd Edition, John Wiley & Sons, New York, N.Y. 1976).

The growth promoting agent moiety of this invention is selected from a group which includes, but is not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox.

The synergistic growth hormone releasing combinations of this invention are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the combinations of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The combinations of this invention can also be employed to investigate the possible negative or positive feedback effects of some of the pituitary hormones, e.g., growth hormone and endorphin peptides, on the pituitary to modify growth hormone release. Of particular scientific importance is the use of these combinations to elucidate the subcellular mechanisms mediating the release of growth hormone.

The combinations of this invention can also be administered to animals, including man, to release growth hormone in vivo. For example, the combinations can be administered to commercially important animals such as swine, cattle, sheep and the like to accelerate and increase their rate and extent of growth, and to increase milk production in such animals. In addition, these combinations can be administered to humans in vivo as a diagnostic tool to directly determine whether the pituitary is capable of releasing growth hormone. For example, the combinations of this invention can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the peptides of Formula I and at least one growth promoting agent in association with a pharmaceutical carrier or diluent. Optionally, the active ingredient of the pharmaceutical compositions can comprise another composition which exhibits a different activity, e.g., an antibiotic or other pharmaceutically active material.

The combinations of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active combination is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of each active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels per active ingredient of between 0.001 to 10 mg/kg. of body weight daily are administered to animals, e.g., mammals, to obtain effective release of growth hormone.

The following examples are provided for the purpose of further illustration only and are not intended to be limitations on the disclosed invention.

EXAMPLE 1

Synthesis of $H_2$-His-D-Trp-D-Phe-Lys-$NH_2$

Para-methylbenzhydrylamine hydrochloride (p-MeBHA.HCl) resin was placed in a reaction vessel. The following procedure, starting at step 6, was then employed in conjunction with a Beckman brand Peptide Synthesizer Model No. 990 in preparing the peptide $H_2$-His-D-Trp-Ala-Trp-D-Phe-Lys-$NH_2$. The synthesis was started at step 6 because there was no amino acid present in the resin and one need only neutralize the resin which was initially in the HCl form.

1. Wash with methylene chloride ($CH_2Cl_2$) for 1.5 minutes, three times.
2. Treat with trifluoroacetic acid-methylene chloride (40% $TFA/CH_2Cl_2$, V/V) containing 0.1% indole for 1.5 minutes.
3. Repeat Step 2 for 20 minutes.
4. Wash with chloroform ($CHCl_3$) for 1.5 minutes, three times.
5. Wash with 30% ethanol-methylene chloride (30% $EtOH/CH_2Cl_2$, V/V) for 1.5 minutes, two times.
6. Wash with $CH_2Cl_2$ for 1.5 minutes, three times.
7. Treat with 10% triethylamine in $CH_2Cl_2$ (10% $TEA/CH_2Cl_2$, V/V) for 1.5 minutes.
8. Repeat Step 7 for 10 minutes.
9. Wash with $CH_2Cl_2$ for 1.5 minutes, three times.
10. Add to the washed resin 2.5 equivalents of the appropriate protected amino acid in dimethyl formamide-methylene chloride ($DMF-CH_2Cl_2$).
11. Add 0.5 N dicyclohexylcarbodiimide in $CH_2Cl_2$ ($DCC/CH_2Cl_2$); more than 2.5 equivalents.
12. Rinse addition funnel with $CH_2Cl_2$ and add rinse to the reaction vessel.
13. Stir the reagents in Steps 10–12 for 2 hours or more.
14. Wash with $CH_2Cl_2$ for 1.5 minutes, three times.
15. Wash with DMF for 1.5 minutes.
16. Wash with $CH_2Cl_2$ for 1.5 minutes, two times.
17. Test by ninhydrin reaction according to the procedure of Kaiser et al., *Annal. Biochem.*, 34:595 (1970).
18. If Step 17 shows complete reaction, repeat the above procedures starting from Step 1 employing the next protected amino acid. If Step 17 shows incomplete reaction, repeat Steps 7–17.

The above procedure was employed using the following sequence of amino acids:

Boc-Lys(ClZ+)
Boc-D-Phe
Boc-Trp
Boc-Ala
Boc-D-Trp
Boc-His(Tos*)

+ClZ denotes o-chloro-benzyloxycarbonyl.
*Tos denotes p-toluenesulfonyl.

After completion of the synthesis of the desired peptide resin, the reaction vessel containing the peptide resin was then placed in a dessicator and dried overnight under a vacuum. The dried peptide resin was removed from the reaction vessel and placed in another vessel suitable for HF cleavage. This latter vessel also contained a magnetic stirring bar. A quantity of anisole sufficient to wet the peptide resin was added to this vessel. The vessel was next connected to an HF line and placed under a vacuum to remove any air therein. The vessel was then cooled to about −78° C. with a dry ice-acetone bath. Doubly distilled HF (about 10 ml/gm of peptide resin) was added to the vessel. The dry ice-acetone bath was then removed from the vessel and replaced by an ice-water bath. The vessel's contents were vigorously stirred for about 45 minutes while the vessel remained immersed in the ice-water bath. Most of the HF in the vessel was then removed by water aspiration. After the majority of HF was removed by water aspiration, the remaining HF and anisole were removed via a vacuum pump.

The vessel's contents were washed with about 100 ml of ether to further remove any residual anisole.

The peptide was removed from the resin by extraction with aqueous acetic acid (aq.HOAc). The aq.-HOAc was lyophilized off to yield a fluffy peptide powder.

The peptide was then purified by partition chromatography or counter current distribution (CCD) employing a butanol:HOAc:water (4:1:5) system. When further purification was necessary, a Pharmacia LH-20 brand chromatography column was also employed.

EXAMPLE 2

In Vitro Growth Hormone Release Study

Female rats of the CD-1 strain were housed in a constant temperature room at 24° C. with 14 hours light and 10 hours darkness. The rats were fed Purina brand rat chow ab libitum. All studies were started between 0800 and 1000 hours.

Pituitaries were removed from 20 day old female rats. In each polytetrafluoroethylene beaker (10 ml) was incubated two pituitaries at 36° C. in 1 ml of lactated Ringer's solution in a Dubnoff Shaker (90 cycles/min.). Three beakers were employed for each dosage shown in Table VI. All medium in each beaker was removed each hour (e.g., $P_1$, $P_2$, $I_3$, $I_4$, $I_5$) and then fresh medium was added back to each beaker. Each medium removed was assayed for GH, in duplicate, by a standard radioimmunoassay (RIA).

The growth hormone agonist of Example 1 was not added to the incubation mediums employed during the first hour of the incubation period ($P_1$) or to the incubation mediums employed during the second hour of the incubation period ($P_2$). The growth hormone agonist of Example 1 was dissolved in dimethylsulfoxide (DMSO; 10:1, agonist:DMSO), added to each incubation medium employed during the third hour of the incubation period ($I_3$), to each medium employed during the fourth hour of the incubation period ($I_4$), and to each medium employed during the fifth hour of the incubation period ($I_5$). The release of growth hormone was recorded as $\Delta GH$ and calculated by subtracting the amount of GH released at $P_2$ from that released at $I_3$, $I_4$, and $I_5$. The agonist activity was determined from the release at $I_3$, $I_4$, and $I_5$. The mean of the $\Delta GH$ values obtained from the three beakers per dosage level measured at $I_3$, $I_4$, and $I_5$ are set forth in Table V.

EXAMPLE 3

In Vitro Growth Hormone Release Study

The procedure set forth in Example 2 was employed in an in vitro growth hormone release study of the growth promoting agent zeranol, $C_{18}H_{26}O_5$, and the results therefrom are set forth in Table VI.

EXAMPLE 4

In Vitro Growth Hormone Release Study

The procedure set forth in Example 2 was employed in an in vitro growth hormone release study of the peptide of Example 1 in combination with the growth promoting agent zeranol, $C_{18}H_{26}O_5$, and the results therefrom are set forth in Table VII. The results set forth in Table VII, when compared to the results set forth in Tables V and VI demonstrate that a combination within the scope of the instant invention can induce a synergistic in vitro release of growth hormone from the pituitary.

TABLE V

IN VITRO GROWTH HORMONE RELEASE

| Zeranol, $C_{18}H_{26}O_5$ | Dosage[2] ΔGH[1] | p Value[4] |
|---|---|---|
| — | −115 ± 49 | — |
| 300 | 83 ± 63 | 0.02 |
| 3,000 | 87 ± 59 | <0.02 |
| 30,000 | 683 ± 187 | <0.001 |
| 100,000 | −133 ± 98 | NS[3] |

[1]The mean of 9 assays given in terms of ng/ml incubation medium ± standard error of the mean (SEM)
[2]Given in terms of ng/ml incubation medium
[3]NS denotes not significant
[4]Comparison of the GH levels in medium containing growth hormone agonist analog to the GH levels in medium without the agonist

TABLE VI

IN VITRO GROWTH HORMONE RELEASE

| $H_2$—His—D-Trp—Ala—Trp—D-Phe—Lys—$NH_2$ | Dosage[2] ΔGH[1] | p Value[3] |
|---|---|---|
| — | −115 ± 49 | — |
| 1 | 887 ± 98 | <0.001 |
| 3 | 821 ± 138 | <0.001 |
| 10 | 2,759 ± 315 | <0.001 |

[1]The mean of 9 assays given in terms of ng/ml incubation medium ± standard error of the mean (SEM)
[2]Given in terms of ng/ml incubation medium
[3]Comparison of the GH levels in medium containing growth hormone agonist analog to the GH levels in medium without the agonist

TABLE VII

IN VITRO GROWTH HORMONE RELEASE

| Zeronol, $C_{18}H_{26}O_5$(A) + $H_2$—His—D-Trp—Ala—Trp—D-Phe—Lys—$NH_2$(B) | Dosage[2] ΔGH[1] | p Value[3] |
|---|---|---|
| — | −309 ± 39 | — |
| 3,000 A + 1B | 2,183 ± 399 | <0.001 |
| 3,000 A + 3B | 2,114 ± 336 | <0.001 |
| 30,000 A + 1B | 2,266 ± 327 | <0.001 |
| 30,000 A + 3B | 2,761 ± 356 | <0.001 |

[1]The mean of 9 assays given in terms of ng/ml incubation medium ± standard error of the mean (SEM)
[2]Given in terms of ng/ml incubation medium
[3]Comparison of the GH levels in medium containing growth hormone agonist analog to the GH levels in medium without the agonist By introducing various other hormones, e.g., somatostatin, testosterone, cortisol, insulin, etc., into the incubation medium of Example 3, one can study what effect these latter hormones have on the regulation of growth hormone secretion.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A composition capable of releasing growth hormone from pituitary comprising an effective amount of a peptide having the formula $H_2$-His-D-Trp-Ala-Trp-D-Phe-Eys-$NH_2$;

and the pharmaceutically acceptable salts thereof; and zeranol, $C_{18}H_{26}O_5$, in a ratio such that, such composition synergistically releases growth hormone from the said pituitary.

2. A method of releasing growth hormone from a pituitary comprising contacting said pituitary with an amount of said composition of claim 1, said amount being effective to synergistically release growth hormone from said pituitary.

3. A method of releasing growth hormone in vitro from a pituitary comprising contacting said pituitary with an amount of said composition of claim 1, said amount being effective to synergistically release growth hormone from said pituitary.

* * * * *